US00PP09002P

United States Patent [19]

Zaiger et al.

[11] Patent Number: Plant 9,002

[45] Date of Patent: Dec. 6, 1994

[54] PEACH TREE "EARLIRICH"

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 4005 California Ave., all of Modesto, Calif. 95358

[21] Appl. No.: 193,544

[22] Filed: Feb. 7, 1994

[51] Int. Cl.[5] ..... A01H 5/00

[52] U.S. Cl. ..... Plt./43.1

[58] Field of Search ..... Plt. 43.1

*Primary Examiner*—James R. Feyrer

[57] ABSTRACT

A new and distinct variety of peach tree with the unique combination of desirable features:

1. Heavy and regular production of large size fruit.
2. Tree ripe fruit with very firm flesh, good shelf life and shipping quality.
3. Fruit coloring two weeks before maturity and having an attractive red skin color.
4. Fruit with good flavor and eating quality.
5. Fruit holding firm on the tree 8–10 days after picking ripe.
6. Relative uniform ripening of the fruit.
7. Having vigorous, upright growth.

1 Drawing Sheet

ORIGIN OF THE VARIETY

The new and distinct variety of peach tree was originated by us in our experimental orchard located near Modesto, Calif., as an open pollinated seedling of Rich Lady Peach (U.S. Plant Pat. No. 7,290). This selection was made from a large number of seedlings that were grown and maintained under careful observation, during which time we recognized the desirable fruit characteristics and selected the variety for asexual reproduction and commercialization.

ASEXUAL REPRODUCTION OF THE VARIETY

Asexual propagation by budding of the new and distinct variety of peach tree was performed by us in our experimental orchard, located near Modesto, Calif. and shows that such reproductions run true to the original tree and all said characteristics are established and transmitted through succeeding propagations.

SUMMARY OF THE VARIETY

The present new and distinct variety of peach tree is of large size, vigorous upright in growth and a productive and regular bearer of large, very firm, yellow flesh, clingstone fruit with good flavor and eating quality. The fruit is further characterized by being relatively uniform in size at maturity, holding firm on the tree 8–10 days after picking ripe, having good handling and shipping quality and being overspread with an attractive red skin color and in comparison to Rich Lady Peach (U.S. Plant Pat. No. 7,290) the new variety is 4 to 5 days earlier in maturity.

BRIEF DESCRIPTION OF THE PHOTOGRAPHS

The accompanying photographic reproductions in color are of typical specimens of the foliage and fruit of our new peach variety; such illustrations being of the upper and lower surface of the leaves, an exterior and sectional view of the fruit divided on its suture plane reveal flesh coloration, pit cavity and a stone remaining in place. The photographic illustrations were taken shortly after being picked at maturity (firm ripe) and the colors are as nearly true as is reasonably possible in a color representation of this type.

DESCRIPTION OF THE VARIETY

The following is a detailed botanical description of the present new variety of peach tree, its flowers, foliage and fruit as based on observations of specimens grown near Modesto, Calif., with color terminology (except those in common terms) referenced to Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Productivity.*—Productive.
- *Bearing.*—Regular.

Trunk:
- *Size.*—Medium to large.
- *Surface.*—Medium shaggy.
- *Color.*—Brown to coffee brown (5-E-6) to (5-E-8).

Branches:
- *Size.*—Medium.
- *Surface.*—Smooth to medium rough — varies with age of growth.
- *Lenticels.*—Numerous. Large size.
- *Color.*—Oak brown to golden brown (5-D-6) to (5-D-7).

Leaves:
- *Size.*—Large. Average length — 6". Average width — $1\frac{5}{8}$".
- *Form.*—Lanceolate. Pointed.
- *Surface.*—Smooth.
- *Margin.*—Crenate.
- *Thickness.*—Medium.
- *Petiole.*—Average length — $\frac{1}{2}$". Medium thickness.
- *Glands.*—Reniform. Number varies from 1 to 4. Average number 2. Positioned on upper portion of petiole and base of leaf blade.
- *Color.*—Upper surface — green to dark green (28-F-6) to (28-F-8) lower surface — dull green to green (28-D-7) to (28-E-7).

Flower buds:
- *Size.*—Large.
- *Form.*—Plump.

*Pubescence.*—Pubescent.

Flowers:

*Size.*—Large — showy.

*Blooming period.*—Mar. 6, 1993 to Mar. 11, 1993. Varies slightly with climatic conditions.

*Color.*—Pink.

*Pollen.*—Present.

Fruit:

*Maturity when described.*—Firm ripe.

*Date of first picking.*—Jun. 6, 1993.

*Date of last picking.*—Jun. 11, 1993. Varies slightly with climatic conditions.

*Size.*—Large — comparatively uniform. Average diameter axially 3". Average transversely in suture plane $3\frac{3}{8}$".

*Form.*—Nearly globose — slightly flattened at stem end. Slight apical tip.

*Suture.*—Very shallow — nearly rounded. Extends from base to apex.

*Ventral surface.*—Nearly rounded — varies from round to slightly lipped.

*Cavity.*—Rounded to slightly elongated in suture plane. Average depth $\frac{1}{2}$". Average breadth 1".

*Base.*—Retuse.

*Apex.*—Slight pistil point.

Flesh:

*Ripens.*—Fairly evenly — only slightly earlier near apex.

*Texture.*—Very firm.

*Juice.*—Moderate.

*Fibers.*—Few tender.

*Flavor.*—Good.

*Eating quality.*—Good.

*Amygdalin.*—Undetected.

*Aroma.*—Moderate.

*Color.*—Yellow to golden yellow (4-A-6) to (4-A-7). Pastel red to light red streaky extending from tip of stone toward apex of fruit. Pit cavity — grayish yellow to grayish orange (4-B-6) to (5-B-6).

Skins:

*Thickness.*—Medium.

*Texture.*—Medium — tenacious to flesh.

*Tendency to crack.*—None.

*Down.*—Moderate — short to medium length.

*Color.*—Yellow ground color (4-A-8) to (5-A-8). Overspread with red to turkish red (10-C-8) to (10-D-8).

Stone:

*Type.*—Clingstone.

*Size.*—Large. Average length — $1\frac{1}{2}$". Average breadth — $1\frac{1}{8}$". Average thickness — $\frac{5}{8}$".

*Form.*—Ovoid.

*Sides.*—Equal to unequal.

*Surface.*—Irregularly furrowed toward apex. Pitted throughout, heavier toward base, pit cavity varies from round to elongated.

*Ridges.*—Mostly rounded, varies from round to narrow along each side of suture.

*Apex.*—Acuminate.

*Base.*—Usually straight, varies from straight to rounded.

*Tendency to split.*—Very slight.

*Color.*—Light brown to brown (6-E-5) to (6-E-8).

Use: Dessert.

*Market.*—Local and long distance.

Keeping quality: Good.

Shipping quality: Good.

The present new variety of peach tree, its flowers, foliage and fruit herein described may vary in slight detail due to soil type, climatic conditions and cultural practices under which the variety may be grown; the present description is that of the variety grown under the ecological conditions prevailing near Modesto, Calif.

We claim:

1. A new and distinct variety of peach tree, substantially as illustrated and described, characterized by its large size, vigorous upright growth, and a productive and regular bearer of large, very firm, yellow flesh, clingstone fruit with good flavor and eating quality; the fruit is further characterized by having an attractive red skin color, good storage and shipping quality, being relatively uniform in size at maturity, holding firm on the tree 8 to 10 days after picking ripe and in comparison to Rich Lady Peach (U.S. Plant Pat. No. 7,290) the new variety is 4–5 days earlier in maturity.

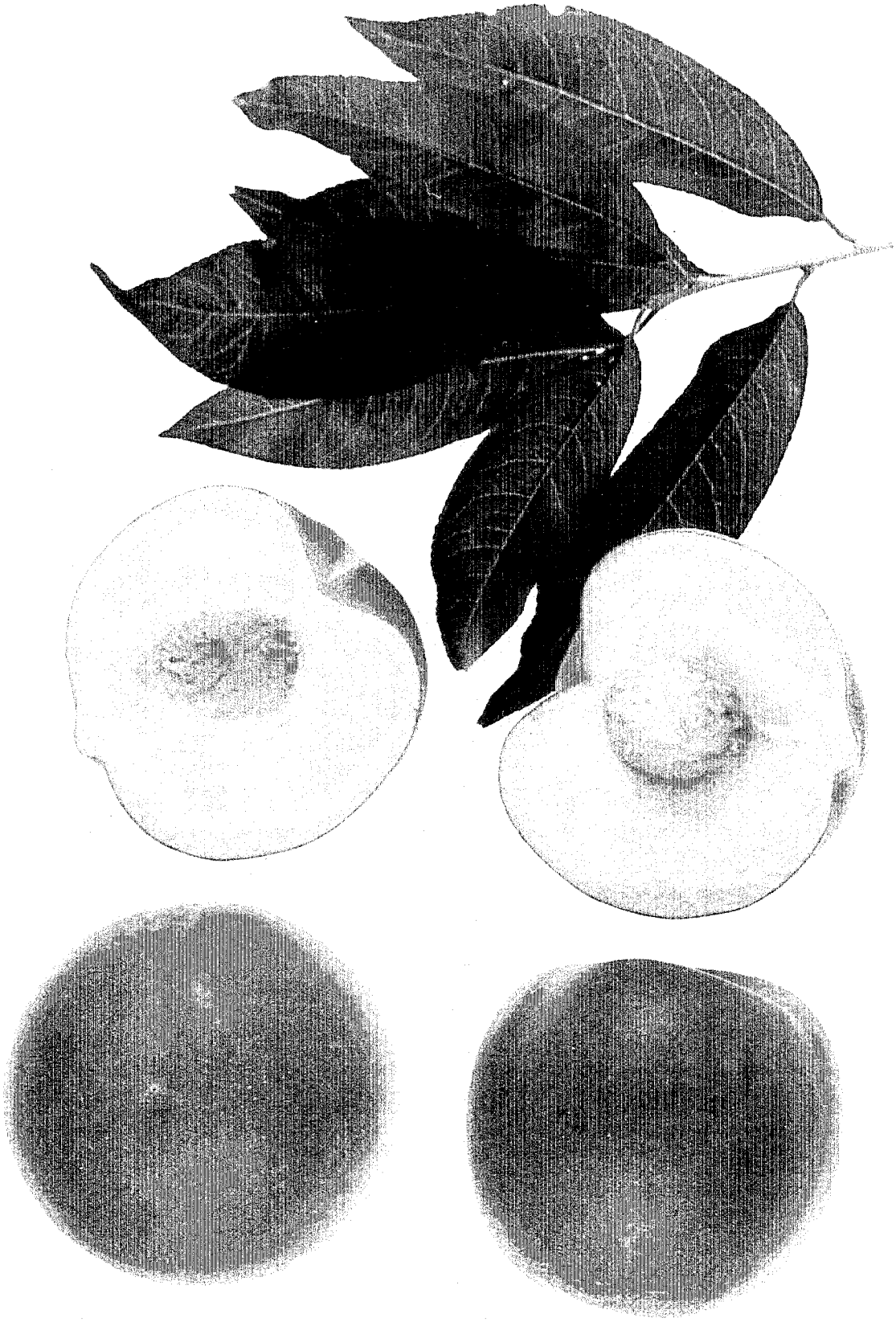

* * * * *